US008093052B2

(12) United States Patent
Fonta et al.

(10) Patent No.: US 8,093,052 B2
(45) Date of Patent: Jan. 10, 2012

(54) SERUM-FREE CULTURE MEDIUM FOR THE PRODUCTION OF RECOMBINANT GONADOTROPINS

(75) Inventors: Jean-Pierre Fonta, Tannay (CH); Paul Ducommun, Lausanne (CH); Véronique Deparis, Clarens (CH)

(73) Assignee: Ares Trading S.A., Aubonne (CH)

( * ) Notice: Subject to any disclaimer, the term of this patent is extended or adjusted under 35 U.S.C. 154(b) by 160 days.

(21) Appl. No.: 11/994,885

(22) PCT Filed: Jul. 4, 2006

(86) PCT No.: PCT/EP2006/063862
§ 371 (c)(1),
(2), (4) Date: Jan. 7, 2008

(87) PCT Pub. No.: WO2007/003640
PCT Pub. Date: Jan. 11, 2007

(65) Prior Publication Data
US 2009/0124006 A1 May 14, 2009

Related U.S. Application Data

(60) Provisional application No. 60/697,077, filed on Jul. 6, 2005.

(30) Foreign Application Priority Data

Jul. 5, 2005 (EP) ..................................... 05106060

(51) Int. Cl.
*C12N 15/85* (2006.01)
*C12P 21/00* (2006.01)
*C07K 1/00* (2006.01)

(52) U.S. Cl. ....... 435/404; 435/70.1; 435/325; 435/405; 530/398

(58) Field of Classification Search ........................ None
See application file for complete search history.

(56) References Cited

U.S. PATENT DOCUMENTS

| | | | |
|---|---|---|---|
| 4,560,655 A | 12/1985 | Baker | |
| 4,657,866 A | 4/1987 | Kumar | |
| 5,021,349 A | 6/1991 | Drouet et al. | |
| 5,122,469 A | 6/1992 | Mather et al. | |
| 6,103,529 A | 8/2000 | Price et al. | |

FOREIGN PATENT DOCUMENTS

| | | |
|---|---|---|
| EP | 0 060 565 | 9/1982 |
| EP | 0 853 945 | 7/1998 |
| EP | 1 221 476 | 7/2002 |
| WO | WO 95/12664 | 5/1995 |
| WO | WO 98/04680 | 2/1998 |
| WO | WO 98/08934 | 3/1998 |
| WO | WO 99/50390 | 10/1999 |

OTHER PUBLICATIONS

Keene et al. (1989), Expression of Biologically Active Human Follitropin in Chinese Hamster Ovary Cells, JBC, vol. 264, No. 9, pp. 4769-4775.*
Altschul, S. F. et al. "Basic Local Alignment Search Tool" *Journal of Molecular Biology*, 1990, pp. 403-410, vol. 215.
Altschul, S. F. et al. "Gapped BLAST and PSI-BLAST: a new generation of protein database search programs" *Nucleic Acids Research*, 1997, pp. 3389-3402, vol. 25, No. 17.
Bassett, R. M. et al. "Continued improvements in the quality and consistency of follitropin alfa, recombinant human FSH" *RBM Online*, 2005, pp. 169-177, vol. 10, No. 2.
Brutlag, D. L. et al. "Improved sensitivity of biological sequence database searches" *CABIOS*, 1990, pp. 237-245, vol. 6, No. 3.
Gonnet, G. H. et al. "Exhaustive Matching of the Entire Protein Sequence Database" *Science*, Jun. 5, 1992, pp. 1443-1445, vol. 256.
Grantham, R. "Amino Acid Difference Formula to Help Explain Protein Evolution" *Science*, Sep. 6, 1974, pp. 862-864, vol. 185, No. 4154.
Henikoff, S. "Performance Evaluation of Amino Acid Substitution Matrices" *Proteins: Structure, Function, and Genetics*, 1993, pp. 49-61, vol. 17.
Higgins, D. G. et al. "Using Clustal for Multiple Sequence Alignments" *Methods in Enzymology*, 1996, pp. 383-402, vol. 266.
Karlin, S. et al. "Methods for assessing the statistical significance of molecular sequence features by using general scoring schemes" *Proc. Natl. Acad. Sci. USA*, Mar. 1990, pp. 2264-2268, vol. 87.
LaPolt, P. S. et al. "Enhanced Stimulation of Follicle Maturation and Ovulatory Potential by Long Acting Follicle-Stimulating Hormone Agonists with Extended Carboxyl-Terminal Peptides" *Endocrinology*, 1992, pp. 2514-2520, vol. 131, No. 6.
Matzuk, M. M. et al. "The Glycoprotein α-Subunit is Critical for Secretion and Stability of the Human Thyrotropin β-Subunit" *Molecular Endocrinology*, 1988, pp. 95-100, vol. 2, No. 2.
Pearson, W. R. et al. "Improved tools for biological sequence comparison" *Proc. Natl. Acad. Sci. USA*, Apr. 1988, pp. 2444-2448, vol. 85.
Saito, Y. et al. "Cell Death Caused by Selenium Deficiency and Protective Effect of Antioxidants" *Journal of Biological Chemistry*, Oct. 2003, pp. 39428-39434, vol. 278, No. 41. Talmadge, K. et al. "The Human Genome Contains Seven Genes for the β-Subunit of Chorionic Gonadotropin but Only One Gene for the β-Subunit of Luteinizing Hormone" *DNA*, 1983, pp. 281-289, vol. 2, No. 4.
Thompson, J. D. et al. "Clustal W: improving the sensitivity of progressive multiple sequence alignment through sequence weighting, position-specific gap penalties and weight matrix choice" *Nucleic Acids Research*, 1994, pp. 4673-4680, vol. 22, No. 22.
"RPMI-1640 Product Information" May 29, 2003, XP002351651.
Yun, Z. et al. "Combined Addition of Glutathione and Iron Chelators for Decrease of Intracellular Level of Reactive Oxygen Species and Death of Chinese Hamster Ovary Cells" *Journal of Bioscience and Bioengineering*, Feb. 2003, pp. 124-127, vol. 95, No. 2.

* cited by examiner

*Primary Examiner* — Christine J Saoud
*Assistant Examiner* — Jegatheesan Seharaseyon
(74) *Attorney, Agent, or Firm* — Saliwanchik, Lloyd & Eisenschenk

(57) ABSTRACT

The present invention is in the field of the manufacture of recombinant proteins. More specifically, it relates to the use of a serum-free culture medium comprising an antioxidant for the production of recombinant dimeric gonadotropins. The antioxidant may be selected from the group consisting of L-glutathione, 2-mercaptoethanol, L-methionine and a combination of ascorbic acid and of (+)-alpha-tocoplierol.

12 Claims, No Drawings

SERUM-FREE CULTURE MEDIUM FOR THE PRODUCTION OF RECOMBINANT GONADOTROPINS

CROSS-REFERENCE TO RELATED APPLICATION

This application is the U.S. national stage application of International Patent Application No. PCT/EP2006/063862 filed Jul. 4, 2006, which claims the benefit of U.S. Provisional Patent Application No. 60/697,077, filed Jul. 6, 2005, the disclosures of which are hereby incorporated by reference in their entireties, including all figures, tables and amino acid or nucleic acid sequences.

FIELD OF THE INVENTION

The present invention is in the field of the manufacture of recombinant proteins. More specifically, it relates to the use of a serum-free culture medium comprising an antioxidant for the production of recombinant dimeric gonadotropins. The antioxidant may be selected from the group consisting of L-glutathione, 2-mercaptoethanol, L-methionine and a combination of ascorbic acid and of (+)-alpha-tocopherol.

BACKGROUND OF THE INVENTION

The present invention relates to production of recombinant Follicle-Stimulating Hormone (FSH). FSH belongs the class of gonadotropins.

FSH is used in the treatment of infertility and reproductive disorders in both female and male patients. FSH is used in female patients in ovulation induction (OI) and in controlled ovarian hyperstimulation (COH), e.g. for assisted reproductive technologies (ART). In a typical treatment regimen for ovulation induction, a patient is administered daily injections of FSH or a derivative thereof (about 75 to 300 IU RFSH/day) for a period of from about 6 to about 12 days. In a typical treatment regimen for controlled ovarian hyperstimulation, a patient is administered daily injections of FSH or a derivative thereof (about 150-600 IU RFSH/day) for a period of from about 6 to about 12 days. FSH is also used to induce spermatogenesis in men suffering from oligospermia. A regimen using 150 IU FSH 3 times weekly in combination with 2'500 IU hCG twice weekly has been successful in achieving an improvement in sperm count in men suffering from hypogonadotrophic hypogonadism. Because of the importance of FSH in the treatment of fertility disorders, the provision of FSH of high stability and of high specific activity is desirable.

In nature, FSH is produced by the pituitary gland. For pharmaceutical use, FSH may be produced recombinantly (rFSH), or it may be isolated from the urine of postmenopausal females (uFSH). The manufacturing process of rFSH necessitates two main steps: cultivation of a genetically engineered cell expressing FSH, and purification of the protein. The protein is then formulated with a pharmaceutically acceptable carrier in order to obtain a pharmaceutical composition.

For culturing cells, in the past the culture medium used to be supplemented with serum, which served as a universal nutrient for the growth and maintenance of all mammalian cell lines. However, the advent of BSE (Bovine Spongiform Encephalopathy), a transmissible neurodegenerative disease of cattle with a long latency or incubation period, has raised regulatory concerns about using animal-derived sera in the production of biologically active products. Therefore, it is currently preferred to produce recombinant proteins using serum-free media. Such media are well known in the art and commercialized by several companies such as, e.g., Sigma, BioWhittaker, Gibco BRL, Cambrex and JRH.

One of the problems encountered when storing rFSH is the presence of oxidized forms of FSH. To partially solve this problem, an antioxidant may be added to the pharmaceutical composition in order to stabilize the FSH protein during storage before administration to the patient in need of treatment. For example, EP 0 853 945 (Skrabanja and Van den Oetelaar, 1998) describes liquid gonadotropin-containing formulations in admixture with a stabilizer such as, e.g., sodium citrate at 25-100 mM and L-methionine at 1-10 mM. It is shown that such formulations allow storage of FSH formulations for longer times. WO 92/15614 (Takruri H., 1992) also relates to a method for inhibiting oxidation of a polypeptide in a liquid or a semi-liquid pharmaceutical composition such as, e.g., a storage medium or an aqueous ophthalmic solution. Specifically, WO 92/15614 shows that an ophthalmic solution or an ophthalmic ointment comprising L-methionine at a concentration of 10 mg/L stabilizes the Human Epidermal Growth Factor. However, the above documents only disclose the use of an antioxidant in a pharmaceutical formulation, and not in a culture medium.

Amino acids and compounds exhibiting antioxidant activity can also be added to culture media, either as nutrients, or for protecting cell lines for cell death. For example, U.S. Pat. No. 4,560,655 discloses a serum-free medium comprising approximately 30 mg/L of L-methionine, said medium being used for cultivation of swine testicle cells, AG14 myeloma cells and murine spleen cells. WO 95/12664 teaches a method by which the disadvantage due to insufficient amounts of various growth-limiting factors, one of them being the L-methionine amino acid, can be overcome for a particular cell line. Specifically, WO 95/12664 teaches a method for adapting the CHO E5F3G cell line, which expresses human M-CSF, to grow at increased cell density. In this method, the CHO E5F3G cells are grown in a medium comprising 104 mg/L of L-methionine (see the Example and Table 2). Yun et al. teaches that the addition of a combination of glutathione and of iron chelators into the culture medium reduces the cell death of CHO cells (Yun et al., 2003). Saito et al. further teaches that various antioxidants may be used in culture media to protect a cell line from cell death (Saito et al., 2003). However, WO 95/12664, U.S. Pat. No. 4,560,655, Yun et al. and Saito et al. are silent on the potential effect (if any) of amino acids, glutathione and iron chelators on the oxidation state of the recombinant protein produced by the cell line. In conclusion, these documents only disclose the use of L-methionine or of glutathione combined to iron chelators for improving the growth and/or the viability of the cultured cells.

WO 99/50390 relates to a culture medium for producing interferon-α from leukocytes, said culture medium comprising methionine. It is demonstrated by HPLC that the quality of the interferon-α protein after purification is improved upon addition of methionine into the culture medium. The inventors of WO 99/50390 hypothesize that this improvement may be due to decreased oxidation of the interferon-α protein. WO 99/50390 further indicates that a too low amount of methionine results in a decreased effect, and that a too high amount causes lower interferon yields. Specifically, WO 99/50390 teaches that a range of about 50 to 100 mg/L is an especially preferred range when producing interferon-α from leukocytes. In addition, WO 99/50390 only contemplates a medium for production of interferon-α, which is a monomeric protein. WO 99/50390 neither mentions nor suggests a medium for production of dimeric hormones such as, e.g., FSH, which is solely secreted upon dimerization (Matzuk et al., 1988).

In summary, none of the documents mentioned above relates to the use of an antioxidant in a serum-free culture medium for reducing the oxidation of dimeric gonadotropins.

SUMMARY OF THE INVENTION

The present invention is based on the unexpected finding that, already during manufacturing of rFSH, oxidized forms of rFSH appear in the surpernatant of the cell culture. Moreover, producing rFSH in serum-free medium leads to higher levels of oxidized forms than production of rFSH in serum-containing medium. In the frame of the present invention, it has surprisingly been found that levels of oxidized forms of rFSH can be reduced not only during storage, but also during the cultivation step. This reduction is achieved without impairing the productivity. The reduction is carried out through the addition of an antioxidant to the culture medium. Specifically, it has been found that supplementing a serum-free medium with either of (i) 2-mercaptoethanol, (ii) a combination of ascorbic acid and (+)-alpha-tocopherol, (iii) L-methionine, or (iv) L-glutathione during cultivation of cells expressing rFSH reduces levels of oxidized forms of rFSH.

Therefore, in a first aspect, the invention relates to the use of a serum-free culture medium for the production of recombinant dimeric gonadotropins characterized in that said culture medium comprises an antioxidant selected from the group consisting of:
  L-glutathione at a concentration ranging from about 1 to about 20 mg/L;
  2-mercaptoethanol at a concentration ranging from about 5 to about 15 mg/L;
  L-methionine at a concentration ranging from about 200 to about 500 mg/L; and
  a combination of ascorbic acid at a concentration ranging from about 10 to about 50 mg/L and of (+)-alpha-tocopherol at a concentration ranging from about 5 to about 25 mg/L.

In a second aspect, the invention relates to a method of reducing the levels of oxidized forms of a recombinant dimeric gonadotropin during its manufacturing process, characterized in that cells expressing said recombinant dimeric gonadotropin are cultivated in a serum-free culture medium comprising an antioxidant.

A third aspect of the invention relates to a serum-free culture medium for the production of recombinant dimeric gonadotropins characterized in that said culture medium comprises an antioxidant selected from the group consisting of:
  L-glutathione at a concentration ranging from about 1 to about 20 mg/L;
  2-mercaptoethanol at a concentration ranging from about 5 to about 15 mg/L;
  L-methionine at a concentration ranging from about 200 to about 500 mg/L; and
  a combination of ascorbic acid at a concentration ranging from about 10 to about 50 mg/L and of (+)-alpha-tocopherol at a concentration ranging from about 5 to about 25 mg/L.

DETAILED DESCRIPTION OF THE INVENTION

The present invention stems from the finding that the levels of oxidized forms of rFSH may be significantly reduced upon cultivation of cells expressing rFSH in a serum-free medium comprising antioxidants. As shown in Example 3, either of (i) 2-mercaptoethanol, (ii) a combination of ascorbic acid and of (+)-alpha-tocopherol, (iii) L-methionine or (iv) L-glutathione are particularly advantageous for reducing the levels of oxidized forms of rFSH during the cultivation process. Importantly, this reduction can be achieved without impairing the viability and the metabolism of the cell, and without impairing the titers of rFSH.

Therefore, a first aspect of the present invention is directed to the use of a serum-free culture medium for the production of recombinant dimeric gonadotropins characterized in that said culture medium comprises an antioxidant selected from the group consisting of:
  L-glutathione at a concentration ranging from about 1 to about 20 mg/L;
  2-mercaptoethanol at a concentration ranging from about 5 to about 15 mg/L;
  L-methionine at a concentration ranging from about 200 to about 500 mg/L; and
  a combination of ascorbic acid at a concentration ranging from about 10 to about 50 mg/L and of (+)-alpha-tocopherol at a concentration ranging from about 5 to about 25 mg/L.

Preferably, the serum-free culture medium in accordance with the present invention comprises L-glutathione at a concentration ranging from about 1, 1.5, 2 to about 4, 5, 6, 7, 8, 9, 10, 15 or 20 mg/L. Most preferably, the serum-free culture medium comprises L-glutathione at a concentration of about 2.5 or 3 mg/L. As used herein, "glutathione" is used interchangeably with "L-glutathione".

Preferably, the serum-free culture medium in accordance with the present invention comprises 2-mercaptoethanol at a concentration ranging from about 5, 6, 7, 8, 9 to about 11, 12, 13, 14 or 15 mg/L. Most preferably, the serum-free culture medium comprises 2-mercaptoethanol at a concentration of about 10 mg/L.

Preferably, the serum-free culture medium in accordance with the present invention comprises a combination of ascorbic acid at a concentration ranging from about 10 to about 50 mg/L and of (+)-alpha-tocopherol at a concentration ranging from about 5 to about 25 mg/L. More preferably, such a medium comprises (+)-alpha-tocopherol at a concentration ranging from about 5, 8, 10 or 12 to about 16, 18, 20, 22 or 25 mg/L, and ascorbic acid at a concentration ranging from about 15, 20 or 25 to about 35, 40 or 45 mg/L. Most preferably, such serum-free culture medium comprises (+)-alpha-tocopherol at a concentration of about 14 mg/L, and ascorbic acid at a concentration of about 30 mg/L. As used herein, "(+)-alpha-tocopherol" is used interchangeably with "vitamin A", and "ascorbic acid" is used interchangeably with "L-ascorbic acid".

Preferably, the serum-free culture medium in accordance with the present invention comprises L-methionine at a concentration ranging from about 200, 205, 210, 215, 220, 225, 230, 235, 240 or 245 mg/L to about 300, 325, 350, 375, 400, 425, 450, 475 or 500 mg/L. Most preferably, the serum-free culture medium comprises L-methionine at a concentration of about 250 mg/L. As used herein, "methionine" is used interchangeably with "L-methionine".

Any serum-free culture medium can be supplemented with antioxidants in accordance with the present invention. Commercially available serum-free media that can be used in accordance with the present invention include, e.g., SFM 90 (JRH, 67350), SFM 90.1 (JRH, 67350), Supmed300 or Supmed300 modified (JRH, 67350), DMEM (Gibco, 7490571), DMEM/F12 (Gibco, 99.5043), SFM CHO 3a (BioWhittaker), CHO PFM (Sigma, C6970), ProCHO 5, EX-CELL media such as EX-CELL 302 (JRH, Catalogue No.

14312-1000M) or EX-CELL 325 (JRH, Catalogue No. 14335-1000M), CHO-CD3 (Sigma, Catalogue No. C-1490), CHO III PFM (Gibco, Catalogue No. 96-0334SA), CHO-S-SFM II (Gibco, Catalogue No. 12052-098), CHO-DHFR (Sigma, Catalogue No. C-8862), ProCHO 5 (Cambrex, Catalogue No. BE12-766Q), SFM4CHO (HyClone, Catalogue No. SH30549.01), Ultra CHO (Cambrex, Catalogue No. 12-724Q), HyQ PF CHO (HyClone, Catalogue No. SH30220.01), HyQ SFX CHO (HyClone, Catalogue No. SH30187.01), HyQ CDM4CHO (HyClone, Catalogue No. SH30558.01), IS CHO-CD (Irvine Scientific, Catalogue No. #91119), IS CHO-V (Irvine Scientific, Catalogue No. #9197) and derivatives thereof. The composition of SFM 90, SFM 90.1, SupMed300, DMEM, DMEM/F12, SFM CHO $3^a$ and CHP PFM, which may be used in accordance with the present invention, is shown in Table 1 below.

TABLE 1

Composition of five commercially available serum-free culture mediums that may be used in the frame of the present invention

| MEDIUM SUPPLIER AND REFERENCE | SFM 90 JRH 67350 mg/l | SFM 90.1 JRH 67350 mg/l | Supmed300 modified JRH 67350 mg/L | DMEM Gibco 7490571 mg/L | DMEM/F12 Gibco 99.5043 mg/L | SFM CHO 3a BioWhittaker mg/l | CHO PFM Sigma C6970 mg/l |
|---|---|---|---|---|---|---|---|
| AMINO ACIDS | | | | | | | |
| L-ALANINE | 23.36 | 23.36 | 23.36 | 84.00 | 4.45 | 26.73 | 15 |
| L-alpha-amino-butyric acid | | | | | | | |
| L-ARGININE | 585.04 | 585.04 | 585.04 | | | 820.4 | 200 |
| L-ARGININE HCL | | | | | 147.50 | | |
| L-ASPARAGINE H2O | 442.07 | 442.07 | 442.07 | | 7.50 | 689.4 | 30 |
| L-ASPARTATE | 341.29 | 341.29 | 341.29 | | 6.65 | 458.93 | 15 |
| L-CYSTEINE | | | | | | | |
| L-CYSTEINE HCl H2O | 92.19 | 92.19 | 92.19 | | 17.56 | 96.68 | 138 |
| L-CYSTINE | | | | | | | |
| L-CYSTINE 2HCl | 23.46 | 23.46 | 23.46 | | 31.29 | | 0 |
| L-GLUTAMATE | 39.34 | 39.34 | 39.34 | | 7.35 | 44.13 | 20 |
| L-GLUTAMINE | 1204.50 | 1204.50 | 1204.50 | 584.00 | 365.00 | 0 | 0 |
| GLYCINE | 247.24 | 247.24 | 247.24 | 30.00 | 18.75 | 317.11 | 20 |
| L-HISTIDINE | | | | | | | |
| L-HISTIDINE HCl, H20 | 70.77 | 70.77 | 70.77 | 42.00 | 31.48 | 109.2 | 100 |
| HYDROXYPROLINE | | | | | | | 0 |
| L-ISOLEUCINE | 248.62 | 248.62 | 248.62 | 105.00 | 54.47 | 299.17 | 140 |
| L-LEUCINE | 368.66 | 368.66 | 368.66 | 105.00 | 59.05 | 490.11 | 150 |
| L-LYSINE | 1880.70 | 1880.70 | 1880.70 | 146.00 | | 582.04 | 200 |
| L-LYSINE-HCL | | | | | 91.25 | | |
| L-METHIONINE | 115.11 | 115.11 | 115.11 | 30.00 | 17.24 | 154.55 | 50 |
| L-ORNITHINE HCL | | | | | | | |
| L-PHENYLALANINE | 37.77 | 37.77 | 37.77 | 66.00 | 35.48 | 33.59 | 100 |
| L-PROLINE | 90.56 | 90.56 | 90.56 | 1500.00 | 17.25 | 140.67 | 200 |
| L-SERINE | 417.79 | 417.79 | 417.79 | 42.00 | 26.25 | 563.66 | 100 |
| SODIUM CYSTINE | | | | 50.21 | | | |
| L-THREONINE | 562.46 | 562.46 | 562.46 | 95.00 | 53.45 | 741.57 | 125 |
| L-TRYPTOPHAN | 56.66 | 56.66 | 56.66 | 16.00 | 9.02 | 91.23 | 100 |
| L-TYROSINE | | | | | | | |
| L-TYROSINE 2Na 2H2O | 145.52 | 145.52 | 145.52 | 90.00 | 55.79 | 172.848 | 120 |
| L-VALINE | 329.66 | 329.66 | 329.66 | 94.00 | 52.85 | 96.9 | 125 |
| SALTS | | | | | | | |
| CaCl2 ANHYDROUS | 87.45 | 87.45 | 87.45 | 199.32 | 116.6 | 200.0085 | 65.9 |
| Ca(NO3)2 4 H2O | | | | | | | 0 |
| CuCl2 | | | | | | | 0.034 |
| CuSO4 5H2O | 0.000938 | 0.000938 | 0.000938 | | 0.0013 | 95 | 0 |
| FeCl3 | | | | | | | 1 |
| FeNO3 9H2O | 0.04 | 0.04 | 0.04 | 0.1 | 0.05 | | 0 |
| FeSO4 7H2O | 0.313 | 0.313 | 0.313 | | 0.417 | 8612 | 0 |
| KCl | 569.25 | 569.25 | 569.25 | 400 | 311.8 | 199.1 | 400 |
| KNO3 | | | | | | | 0 |
| K3PO4 | | | | | | | 0 |
| MgCl2 ANHYDROUS | 107.29 | 107.29 | 107.29 | | 28.64 | | 155 |
| MgSO4 ANHYDROUS | 36.63 | 36.63 | 36.63 | 97.6 | 48.84 | 77.32 | 0 |
| MnCl2 | | | | | | | 0 |
| MnSO4 | 0.17 | 0.17 | 0.17 | | | | 0 |
| MnSO4 H2O | | | | | | | |
| Na2HPO4 | | | | | 71.02 | | |
| Na2HPO4 H2O | 53.4 | 53.4 | 53.4 | | | 66.206 | 142 |
| Na2SeO3 | 0.324 | 0.324 | 0.324 | | | | 0.001 |
| NaCl | 5520 | 5520 | 5520 | 6400 | 6995.5 | 3300 | 5000 |
| NaH2PO4 ANHYDROUS | 46.88 | 46.88 | 46.88 | 108.5115 | | 125 | 0 |
| NaH2PO4 H2O | | | | | 62.5 | | |
| NaHCO3 | 0.0375 | 0.0375 | 0.0375 | | | | 0 |
| ZnCl2 | | | | | | | 8.18 |

TABLE 1-continued

Composition of five commercially available serum-free culture mediums that may be used in the frame of the present invention

| MEDIUM SUPPLIER AND REFERENCE | SFM 90 JRH 67350 mg/l | SFM 90.1 JRH 67350 mg/l | Supmed300 modified JRH 67350 mg/L | DMEM Gibco 7490571 mg/L | DMEM/F12 Gibco 99.5043 mg/L | SFM CHO 3a BioWhittaker mg/l | CHO PFM Sigma C6970 mg/l |
|---|---|---|---|---|---|---|---|
| $ZnSO_4$ $7H_2O$ | 0.31275 | 0.31275 | 0.31275 | | 0.432 | 3.329 | 0 |
| TRACE ELEMENTS | | | | | | | |
| $AgNO_3$ | 0.00017 | 0.00017 | 0.00017 | | | | |
| $AlCl_3$ $6H_2O$ | 0.00217 | 0.00217 | 0.00217 | | | | |
| $Ba(C_2H_3O_2)_2$ | 0.00255 | 0.00255 | 0.00255 | | | | |
| $CdCl_2$ ANHYD. | 0.001806 | 0.001806 | 0.001806 | | | | |
| $CdSO_4$ | | | | | | | |
| $CoCl_2$ | 0.00238 | 0.00238 | 0.00238 | | | | |
| $CoCl_2$ $6H_2O$ | | | | | | | |
| $Cr(SO_4)_3$ | | | | | | | |
| $CrCl_3$ | | | | | | | |
| $CrCl_3$ $6H_2O$ | 0.00039 | 0.00039 | 0.00039 | | | | |
| $GeO_2$ | 0.00053 | 0.00053 | 0.00053 | | | | |
| $H_2SeO_3$ | | | | | | | |
| KBr | 0.00012 | 0.00012 | 0.00012 | | | | |
| KI | 0.00017 | 0.00017 | 0.00017 | | | | |
| LiCl | | | | | | | |
| $(NH_3)_2Mo$ $O_4$ $7H_2O$ | | | | | | | |
| $Na_2SiO_3$ $9H_2O$ | 0.14 | 0.14 | 0.14 | | | | |
| $Na_6Mo_7O_{24}$ | | | | | | | |
| NaF | 0.0042 | 0.0042 | 0.0042 | | | | |
| $(NH_3)_6Mo_7O_{24}$ $4H_2O$ | 0.00124 | 0.00124 | 0.00124 | | | | |
| $NH_4VO_3$ | 0.00065 | 0.00065 | 0.00065 | | | | |
| $NiCl_2$ | | | | | | | |
| $NiSO_4$ $6H_2O$ | 0.00013 | 0.00013 | 0.00013 | | | | |
| RbCl | 0.00121 | 0.00121 | 0.00121 | | | | |
| $SnCl_2$ | | | | | | | |
| $SnCl_2$ $2H_2O$ | 0.00012 | 0.00012 | 0.00012 | | | | |
| $TiCl_2$ | | | | | | | |
| $ZrOCl_2$ $8H_2O$ | 0.00322 | 0.00322 | 0.00322 | | | | |
| CARBOHYDRATES | | | | | | | |
| L-GLUCOSE | 3225 | 3225 | 3225 | 4500 | 3.5 | 4300 | 4500 |
| L-FRUCTOSE | | | | | | | 0 |
| L-MANNOSE | | | | | | | 0 |
| VITAMINS | | | | | | | |
| ASCORBIC ACID | | | | | | | |
| BIOTIN | 2.02 | 2000 | 2000 | | 0.0035 | 0.032 | 0.5 |
| CHOLINE CHLORIDE | 40.13 | 40.13 | 40.13 | 4 | 8.98 | 86.88 | 70 |
| CYANOCOBALAMIN (B12) | 3.57 | 3.57 | 3.57 | | 0.68 | 1.288 | 6.8 |
| D Ca PANTHOTENATE | 4.76 | 4.76 | 4.76 | 4 | 2.24 | 3.544 | 20 |
| DL ALPHA LIPOIC ACID | | | | | | | 0 |
| DL ALPHA TOCOPHEROL ACETATE | 0.7 | 0.7 | 0.7 | | | | 0 |
| FOLATE | 6.9 | 6.9 | 6.9 | 4 | 2.65 | 13.002 | 20 |
| I-INOSITOL | | 53.9 | 53.9 | 7.2 | | | |
| MYO-INOSITOL | 53.9 | | | | 12.6 | 69.23 | 90 |
| NIACINAMIDE | 3.6 | 3.6 | 3.6 | | 2.02 | | 20 |
| NICOTINAMIDE | | | | 4 | | 2.0898 | |
| PYRIDOXAL HCl | 3.5 | 3.5 | 3.5 | 4 | | | 0 |
| PYRIDOXINE HCl | 0.163 | 0.163 | 0.163 | | 0.031 | 2.3651 | 20 |
| RIBOFLAVINE | 0.45 | 0.45 | 0.45 | 0.4 | 2 | 0.5128 | 0.188 |
| SODIUM PANTHOTHENATE | | | | | | | |
| THIAMINE HCl | 4.3 | 4.31 | 4.31 | 4 | 2.17 | 2.471 | 10.85 |
| TOCOPHEROL | | | | | | 24 | |
| LIPIDS | | | | | | | |
| ARACHIDONIC ACID | 0.02 | 20 | 20 | | | | 0.595 |
| CHOLESTEROL | 2.2 | 2.2 | 2.2 | | | | 0 |
| COD LIVER OIL | | | | | | | 0 |
| LAURIC ACID | | | | | | | 0.595 |
| LINOLEIC ACID | 0.321 | 0.321 | 0.321 | | 0.042 | 700 | 0.595 |
| LINOLENIC ACID | 0.1 | 0.1 | 0.1 | | | | 0 |
| LIPOIC ACID | | | | | 0.105 | 0.788 | |
| MYRISTIC ACID | 0.1 | 0.1 | 0.1 | | | | 0.595 |
| Na LINOLEATE | | | | | | 0.273 | |
| OLEIC ACID, Na salt | 0.108 | 0.108 | 0.108 | | | | 0.595 |

TABLE 1-continued

Composition of five commercially available serum-free culture mediums that may be used in the frame of the present invention

| MEDIUM SUPPLIER AND REFERENCE | SFM 90 JRH 67350 mg/l | SFM 90.1 JRH 67350 mg/l | Supmed300 modified JRH 67350 mg/L | DMEM Gibco 7490571 mg/L | DMEM/F12 Gibco 99.5043 mg/L | SFM CHO 3a BioWhittaker mg/l | CHO PFM Sigma C6970 mg/l |
|---|---|---|---|---|---|---|---|
| PALMITIC ACID | 0.1 | 0.1 | 0.1 | | | | 0 |
| PALMITOLEIC ACID | 0.1 | 0.1 | 0.1 | | | | 0 |
| STEARIC ACID | 0.1 | 0.1 | 0.1 | | | | 0 |
| THIOCTIC ACID | | | | | | | 0 |
| MISCELLANEOUS | | | | | | | |
| 2-MERCAPTOETHANOL | | | | | | | |
| CITRIC ACID (Na)3 | | | | | | | 59 |
| CYCLODEXTRIN | | | | | | | |
| EDTA (Na)4 | | | | | | | 10 |
| FeNH3 CITRATE | | | | | | | |
| FERRIC CITRATE | 122.500 | 12.250 | | | | | |
| HYPOXANTHINE | 14.550 | 14.550 | 14.550 | | 2.390 | | |
| L-GLUTHATHIONE | | | | | | | |
| MOPS | | | | | | | |
| NaPYRUVATE | 288.750 | 288.750 | 288.750 | 110.000 | 55.000 | 421.67 | 110 |
| PABA | | | | | | | |
| PHENOL RED | | | | | | 15 | 0 |
| PUTRESCINE, 2HCl | 0.423 | 0.423 | 0.423 | | 0.081 | 0.9763 | 4 |
| THYMIDINE | 1.916 | 1.916 | 1.916 | | 0.365 | | |
| DETERGENTS | | | | | | | |
| ETHANOLAMINE HCl | 9.79 | 9.79 | 9.79 | | | | |
| FB | | | | | | | |
| PLURONIC F68 | 1.00E+03 | 1.00E+03 | | | | 0 | 1000 |
| TWEEN 80 | | | | | | | |
| COMPLEMENTS | | | | | | | |
| 2 HP-BETA-CYCLODEXTRIN | | | | | | | |
| AURINTRICARBOXYLIC ACID | | | | | | | 6.3 |
| FETUIN | | | | | | | |
| HYDROCORTISONE | 0.5 | 0.5 | 0.5 | | | | 3.6 |
| HyPep 4601 | | | | | | | 2500 |
| Hy-Soy | | | | | | 0.2 | 1000 |
| IGF-1 | | | | | | 5 | 2 |
| INSULIN | 10 | 1 | | | | | |
| LIPOSOMES | | | | | | 1200 | |
| METHYL-BETA-CYCLODEXTRIN | | | | | | | 115.85 |
| PRIMATONE | | | | | | | |
| TRANSFERRIN | | | | | | | |
| Additives | | | | | | | |
| GLUTAMINE | | | | | | | |
| Na2CO3 | | | | 1250 | | 2100 | |
| HEPES | 2234.250 | 2234.250 | 2234.250 | 4766 | | 5000 | 3574.5 |
| pH specified | 7 | | | 7.2-7.4 | | | |
| TOTAL (g/L) | 18545.60 | 20444.32 | 19431.07 | 16176.34 | 8840.29 | 27556.20 | 17292.18 |

In a preferred embodiment of the present invention, the serum-free culture medium is a chemically defined medium, i.e., a medium prepared from purified ingredients and therefore whose exact composition is known. Specifically, chemically defined media do neither contain animal derived components nor undefined hydrolysates.

Gonadotropins that may be produced in accordance with the present invention include the luteinizing hormone (LH; OMIM Accession No. 152780), the follicle-stimulating hormone (FSH; OMIM Accession No. 136530), the chorionic gonadotropin, (CG; OMIM Accession No. 118860) and the thyroid-stimulating hormone (TSH; OMIM Accession No. 188540). The gonadotropins are dimeric hormones. Each of these hormones consists of a noncovalent dimer of alpha and beta subunits. The alpha subunit is the same for all 4 hormones (OMIM Accession No. 118850), and the beta subunits define the endocrine function of the dimer (Talmadge et al., 1983).

In a most preferred embodiment of the present invention, the gonadotropin is human FSH. As used herein, the term "FSH" relates to a dimeric protein comprised of an alpha subunit corresponding to SwissProt Accession No. P01215 and of a beta subunit corresponding to SwissProt Accession No. P01225. Since FSH is a soluble, secreted protein, it is released into the cell culture supernatant, either by means of its natural signal peptide, or by means of a heterologous signal peptide, i.e. a signal peptide derived from another secreted protein which may be more efficient in the particular expression system used.

The term FSH further includes splice variants, allelic variants, muteins, functional derivatives, active fractions, fused proteins and circularly permutated proteins of a dimeric protein comprised of an alpha subunit corresponding to SwissProt Accession No. P01215 and of a beta subunit corresponding to SwissProt Accession No. P01225.

As used herein the term "mutein" refers to analogs of FSH, in which one or more of the amino acid residues of a natural FSH or viral FSH are replaced by different amino acid residues, or are deleted, or one or more amino acid residues are added to the natural sequence of FSH, without changing considerably the activity of the resulting products as compared with the wild FSH. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes an FSH under stringent conditions. The term "stringent conditions" refers to hybridization and subsequent washing conditions, which those of ordinary skill in the art conventionally refer to as "stringent" (see, e.g., Ausubel et al., Current Protocols in Molecular Biology, supra, Interscience, N.Y., §§6.3 and 6.4, 1987, 1992). Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

In a preferred embodiment, an FSH mutein has at least 40% identity with the sequence of a naturally occurring FSH. More preferably, it has at least 50%, 55%, 60%, 65%, 70%, 75%, 80%, 85% or, most preferably, at least 90%, 95%, 96%, 97%, 98% or 99% identity thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called "global alignment"), that is particularly suitable for sequences of the same or very similar length, or over shorter, defined lengths (so-called "local alignment"), that is more suitable for sequences of unequal length. In the frame of the present invention, the "% of identity" refers to the global percent of identity that has been determined over the whole length of each of the sequences being compared.

Known computer programs may be used to determine whether any particular polypeptide is a percentage identical to a sequence of the present invention. Such algorithms and programs include, e.g. TBLASTN, BLASTP, FASTA, TFASTA, and CLUSTALW (Altschul et al., 1990; Altschul et al., 1997; Higgins et al., 1996; Pearson and Lipman, 1988; Thompson et al., 1994). Protein and nucleic acid sequence homologies are preferably evaluated using the Basic Local Alignment Search Tool ("BLAST"), which is well known in the art (Altschul et al., 1990; Altschul et al., 1997; Karlin and Altschul, 1990).

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. The scoring matrix used may be the BLOSUM62 matrix (Gonnet et al., 1992; Henikoff and Henikoff, 1993). The PAM or PAM250 matrices may also be used (See, e.g., Schwartz and Dayhoff, eds., (1978) Matrices for Detecting Distance Relationships: Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (Karlin and Altschul, 1990). The BLAST programs may be used with the default parameters or with modified parameters provided by the user.

A preferred method for determining the best overall match between a query sequence (a sequence of the present invention) and a subject sequence, also referred to as a global sequence alignment, can be determined using the FASTDB computer program based on the algorithm of Brutlag (Brutlag et al., 1990). In a sequence alignment the query and subject sequences are both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group=25 Length=0, Cutoff Score=1, Window Size=sequence length, Gap Penalty=5, Gap Size Penalty=0.05, Window Size=247 or the length of the subject amino acid sequence, whichever is shorter.

If the subject sequence is shorter than the query sequence due to N- or C-terminal deletions, not because of internal deletions, the results, in percent identity, must be manually corrected because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, that are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence.

For example, a 90 amino acid residue subject sequence is aligned with a 100-residue query sequence to determine percent identity. The deletion occurs at the N-terminus of the subject sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%.

Preferred changes for muteins in accordance with the present invention are what are known as "conservative" substitutions. Conservative amino acid substitutions of FSH may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

The term "fused protein" of FSH refers to a polypeptide comprising FSH, a mutein or a fragment thereof, fused with another protein, which, e.g., has an extended residence time in body fluids. FSH may for example be fused to an immunoglobulin or a fragment thereof such as an immunoglobulin Fc portion. The sequence of mature FSH may also be fused to a signal peptide and/or to a leader sequence allowing enhanced secretion.

In a preferred embodiment of the invention, the FSH beta-subunit or a fragment thereof is fused to the carboxyl-terminal peptide (CTP) of hCG beta-subunit. The resulting protein has identical in vitro receptor-binding and biological activities as FSH, but an increased circulating half-life (LaPolt et al., 1992).

As "active fraction" of FSH or muteins thereof, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to FSH.

"Functional derivatives" of FSH as used herein, cover derivatives of FSH or a mutein thereof, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of the gonadotropin, and do not confer toxic properties on compositions containing it. These derivatives may, for example, include polyethylene glycol side-chains, which may mask antigenic sites and extend the residence of FSH in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties. In a preferred embodiment, the functional derivative corresponds to an FSH molecule displaying additional glycosilation.

The term "salts" of FSH herein refers to both salts of carboxyl groups and to acid addition salts of amino groups of FSH. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the gonadotropin.

As used herein, the term "recombinant dimeric gonadotropin" refers to a gonadotropin that has been produced upon cultivation of a genetically engineered cell. The gonadotropin may be produced in a cell of any origin. The genetically engineered cell expressing a dimeric gonadotropin expressed both subunits of said dimeric gonadotropin.

As used herein, the term "genetically engineered cell" refers to a cell in which exogenous DNA has been introduced in such a way as to allow expression of both subunits of the desired gonadotropin. The exogenous DNA may comprise a sequence coding for the subunits of the desired gonadotropin. Alternatively, the exogenous DNA may comprise a sequence activating expression of the endogenous sequence coding for the subunits of the desired gonadotropin (see, e.g., WO 91/09955).

The cells may be of, e.g., animal, insect or microbial origin. As used herein, the term "animal cell" includes human and non-human mammalian cells, non-mammalian cells and hybridomas. Examples of mammalian cells in which a recombinant dimeric gonadotropin can be produced include, e.g., 3T3 cells, COS cells, human osteosarcoma cells, MRC-5 cells, BHK cells, VERO cells, CHO cells, rCHO-tPA cells, rCHO—Hep B Surface Antigen cells, HEK 293 cells, rHEK 293 cells, rC127—Hep B Surface Antigen cells, Normal Human fibroblast cells, Stroma cells, Hepatocytes cells, PER.C6 cells and human permanent amniocytic cells. Examples of hybridomas in which a recombinant dimeric gonadotropin can be produced include, e.g., DA4.4 cells, 123A cells, 127A cells, GAMMA cells and 67-9-B cells.

In the frame of the present invention, it is preferred to cultivate a Chinese Hamster Ovary cell (CHO cell).

A second aspect of the present invention is directed to a method of reducing the levels of oxidized forms of a recombinant dimeric gonadotropin during its manufacturing process, characterized in that cells expressing said recombinant dimeric gonadotropin are cultivated in a serum-free culture medium comprising an antioxidant.

As used herein, the term "oxidized forms" refers to a polypeptide in which an oxidant has caused oxidation of one or more amino acid residues. Such forms can be detected by, e.g., HPLC as described in Example 2.1 for FSH.

The cultivation may be carried out in any suitable environment, such as Petri dishes, T-flasks or roller bottles, but preferably in vessels having greater volumes such as, e.g., a bioreactor.

The cultivation step comprises the following steps:
An inoculation of said cells in said serum-free culture medium;
A growth phase; and
A production phase.

The growth phase is the part of the cell culture process in which process parameters are set in order to support cell growth. Once the desired cell density has been reached, the cell culture is usually switched into a production phase, in which process parameters are set in order to support cell productivity. The process parameters may be the same during the growth phase and the production phase. During the production phase, the cell concentration has preferably a value comprise within a range of $1.10^6$ to $5.10^7$ cells/mL, e.g., of about $1.10^6$, $5.10^6$, $10^7$ or $5.10^7$ cells/mL. Most preferably, said cell is a CHO cell.

In one embodiment, the antioxidant is added to the serum-free culture medium before inoculation of the cells. In another embodiment, the antioxidant is added to the serum-free culture medium shortly after inoculation of the cells (e.g., not more than 24 h after inoculation).

Preferably, the manufacturing process comprises the step of collecting the medium comprising the recombinant dimeric gonadotropin.

In a preferred embodiment, the manufacturing process further comprises purifying the recombinant dimeric gonadotropin. Methods of purifying gonadotropins are well-known in the art. FSH may for example be purified as described in EP 04 105 639.1, WO 98/20039, WO 00/63248 or WO 88/10270.

In a further preferred embodiment, the manufacturing process further comprises formulating the recombinant dimeric gonadotropin with a pharmaceutically acceptable carrier to obtain a pharmaceutical composition.

The term "Pharmaceutically acceptable carrier", as used herein, is meant to encompass any carrier that does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The pharmaceutical composition formulated according to the invention may then be administered to an individual in a variety of ways. The routes of administration include intradermal, transdermal (e.g. in slow release formulations), intramuscular, intraperitoneal, intravenous, subcutaneous, oral, intracranial, epidural, topical, rectal, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles. For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

In a preferred embodiment of the present invention, the method of reducing the levels of oxidized forms of a recombinant dimeric gonadotropin during its manufacturing process is characterized in that at least two, three, four, five or six steps of said manufacturing process are carried out in the presence of an antioxidant. Preferably, all steps of said manufacturing process are carried out in the presence of an antioxidant, i.e., the whole manufacturing process is carried out in the presence of an antioxidant.

For example, the method of reducing the levels of oxidized forms of a recombinant dimeric gonadotropin during its manufacturing process may comprise the steps of:

Cultivating cells expressing said recombinant dimeric gonadotropin in a serum-free culture medium comprising an antioxidant;

Collecting the medium comprising said recombinant dimeric gonadotropin; and

Purifying said recombinant dimeric gonadotropin in the presence of an antioxidant.

Preferably, the method of reducing the levels of oxidized forms of a recombinant dimeric gonadotropin during its manufacturing process further comprises the step of formulating said recombinant dimeric gonadotropin into a pharmaceutical composition comprising an antioxidant.

The antioxidant may be the same at all steps of the manufacturing process wherein an antioxidant is used. Alternatively, different antioxidants may be used at the cultivation step, the purification step and/or the formulation step. Numerous compounds having an antioxidant effect are known in the art. These compounds include, e.g., cysteine, ascorbic acid, L-methionine, L-glutathione, 2-mercaptoethanol, alpha-tocopherol and derivatives thereof, BO-653, t-butyl-4-methoxy-phenol, 2,6-bis(1,1-dimethylethyl)-4-methyl phenol; potassium or sodium bimeta-bisulfite, sodium bisulfite, histidine, taurine, glycine, alanine, carnosine, anserine and 1-methylhistidine.

A third aspect of the present invention is directed to a serum-free culture medium for the production of recombinant dimeric gonadotropins characterized in that said culture medium comprises an antioxidant selected from the group consisting of:

L-glutathione at a concentration ranging from about 1 to about 20 mg/L;

2-mercaptoethanol at a concentration ranging from about 5 to about 15 mg/L;

L-methionine at a concentration ranging from about 200 to about 500 mg/L; and a combination of ascorbic acid at a concentration ranging from about 10 to about 50 mg/L and of (+)-alpha-tocopherol at a concentration ranging from about 5 to about 25 mg/L.

Serum-free culture media usually comprise water, an osmolarity regulator, a buffer, an energy source, amino acids, an inorganic or recombinant iron source, a recombinant or synthetic growth factor, and optionally non-ferrous metal ions, vitamins and cofactors. For example, any of the commercially available serum-free media listed above may be modified in accordance with the present invention.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Example 1

Cell Culture Process 1.1. Cell Lines and Media

All experiments were performed with a CHO cell line expressing both subunits of human FSH. The produced protein is a dimeric gonadotropin further referred to as rFSH. The alpha subunit corresponds to SwissProt Accession No. P01215 and the beta subunit corresponds to SwissProt Accession No. P01225.

The medium used for cell cultivation was a basic serum-free medium (SFM) designed for cultivation of CHO cells. The SFM medium was supplemented with the antioxidant to be tested as detailed in Example 3. The initial concentration of the antioxidants to be tested in the basic SFM is shown in Table I.

TABLE I

Initial concentration of antioxidants in the basic serum-free medium

| Compound | Initial concentration in basic SFM |
| --- | --- |
| L-cysteine | 138 mg/L |
| Cystine-2HCL | 0 mg/L |
| N-acetyl-L-cysteine (NAC) | 0 mg/L |
| L-ascorbic acid | 0 mg/L |
| L-methionine | 50 mg/L |
| L-glutathione | 0 mg/L |
| 2-mercaptoethanol | 0 mg/L |
| (+)-alpha-tocopherol | 0 mg/L |

1.2. Inoculation, Growth and Production Conditions

The culture process, also referred to as "run", comprises an inoculation step, a growth phase and a production phase. Five different runs, referred to as runs 1, 2, 3, 4 and 5, were performed.

At least $2.4 \cdot 10^9$ viable rFSH-producing cells were transferred to a 15 L bioreactor with an effective working volume of 11 L (newMBR, Zürich) comprising microcarriers. Immediately after seeding followed a batch phase that lasted for two or three days. The bioreactor was then continuously fed with SFM to a dilution rate of 1 day$^{-1}$ and to a perfusion rate at 11 L·day)$^{-1}$.

Growth phase and production phase were performed at the same pH and temperature (37° C., pH=7). The Dissolved Oxygen (DO) was maintained at 50% air saturation during the whole run.

Example 2

Analytical Methods 2.1. Determination of Oxidized Forms of rFSH

Oxidized forms were determined by RP-HPLC on crude harvest as described by Bassett and Driebergen (Bassett and Driebergen, 2005).

The percentages of oxidized forms were normalized using the percentage of oxidized forms obtained with L-cysteine at 280 mg/L in run 2 as a reference (i.e., the percentages of oxidized forms were divided by 23.4%).

2.2. Measurement of the Total Viable Cell Concentration

The total viable cell concentration is defined as the sum of the concentration of cells attached on microcarriers and the concentration of viable cells in suspension. The concentration of cells attached on microcarriers was determined using the crystal violet nuclei counting method (Fluka 61135). The concentration of viable cells in suspension was determined using the Trypan blue exclusion method (Sigma T-8154).

The Total Viable Cells Ratio (TVC Ratio) for was calculated as follows: [total viable cell concentration, end of test]/[total viable cell concentration, start of test] wherein the start of test is defined as the day at which a new antioxidant is introduced in the culture, and the end of test is defined as the day before the next antioxidant is introduced in the culture.

2.3. Measurement of the rFSH Titers

The rFSH titer was measured by an immunofluorimetric assay, using the Delphia hFSH kit from Wallac-ADL (Cat. No. A017-201).

2.4. Measurement of the Glucose Consumption Rate (GCR)

The glucose consumption rate (GCR), expressed in gram per liter and per day, was calculated as follows: $GCR=(G_0-G_t)D_t+(G_{t-1}-G_t)$ G stands for "Glucose concentration" and D stands for "dilution rate". The indexes refer to the following:
0: in feed SFM;
t: measured at time t; and
t−1: measured at time t−1

Example 3

Effect of Various Antioxidants

In order to reduce the level of oxidized forms obtained with the serum-free process, two 15 L runs (runs 1 and 2) were performed testing the effect of various antioxidants. A run without addition of any antioxidant was performed as a control (run 3).

SFM was supplemented with several antioxidant or combination of antioxidants in order to reach the final concentration shown in Table II. Each antioxidant or combination of antioxidants was tested for a period of about ten days. The first day of the test, the volume of antioxidant solution necessary to reach the set-point was added. Every day thereafter, a certain amount of antioxidant was washed out from the bioreactor by perfusion and replaced by one time addition (for a dilution rate of 1 d$^{-1}$, 63.2% of the bioreactor volume was renewed every 24 h and this represents the amount of antioxidant to be replaced every day). At the end of the test period, the antioxidant was washed out from the bioreactor by perfusion, and replaced by another antioxidant to be tested.

The percentage of oxidized forms of rFSH was measured at the end of each test (table II). A normalized value inferior to 1.0 indicates that the tested antioxidant is more efficient than L-cysteine for diminishing the levels of rFSH oxidized forms.

The total viable cell concentration, the GCR and the rFSH titers were measured daily. Table II indicates the total viable cells ratio (TVC ratio). A TVC ratio superior or equal to 1.0 indicates that the tested antioxidant has no toxic effect on the cells.

TABLE II

Effect of antioxidants on the oxidized forms of rFSH

| Working days (WD) at which the antioxidant was tested | WD at which the oxidized forms were measured | Antioxidant | Mean concentration (mg/L) | % of oxidized forms | oxidized forms (normalized value) | TVC Ratio |
|---|---|---|---|---|---|---|
| Run 1 | | | | | | |
| WD10 to WD20 | WD20 | L-cysteine | 280 | 21.5 | 0.92 | 8.6 |
| WD20 to WD30 | WD30 | L-ascorbic acid | 10 | 17.3 | 0.74 | 1.3 |
| WD30 to WD40 | WD38 | L-methionine | 186 | 14.3 | 0.61 | 1.4 |
| WD40 to WD50 | WD50 | L-glutathione | 3 | 14.2 | 0.61 | 1.2 |
| WD50 to WD60 | WD59 | 2-mercaptoethanol | 10 | 12.3 | 0.53 | 0.8 |
| WD60 to WD70 | WD70 | L-methionine | 734 | 14.0 | 0.60 | 1.0 |
| WD70 to WD80 | WD79 | L-Ascorbic acid + (+)-alpha-tocopherol | 30 14 | 14.8 | 0.63 | 1.0 |
| Run 2 | | | | | | |
| WD0 to WD20 | WD20 | L-cysteine | 280 | 23.4 | 1.00 | 6.3 |
| WD20 to WD30 | WD30 | Cysteine 2HCl | 50 | 17.3 | 0.74 | 1.4 |
| WD30 to WD40 | WD38 | N-acetyl-L-cysteine | 260 | 18.1 | 0.77 | 1.3 |
| WD40 to WD50 | WD50 | L-cysteine | 350 | 20.5 | 0.88 | 1.0 |
| WD50 to WD56 | WD56 | L-Cysteine + L-ascorbic acid + 2-mercaptoethanol | 280 10 10 | 19.0 | 0.81 | 1.0 |

The results shown in table II indicate that 2-mercaptoethanol, a combination of ascorbic acid and (+)-alpha-tocopherol, L-methionine, and L-glutathione are the best antioxidants for obtaining low levels of rFSH oxidized forms.

A TVC ratio total viable cells inferior to 1.0 is obtained only in the case of 2-mercaptoethanol. Therefore, all the antioxidants tested in Runs 1 & 2 but 2-mercaptoethanol are non-toxic. In addition, measurement of the GCR and of the rFSH titers showed that none of the various antioxidants had any major impact on metabolism and productivity patterns (data not shown).

L-methionine and L-glutathione were chosen for further optimization of the production process. One run (run 3) was performed to test various concentrations of L-glutathione (from 1 to 20 mg/L), and one run (run 4) was performed to test various concentrations of L-methionine (from 0.25 to 3 g/L) and. Run 3, testing L-glutathione was prematurely stopped at production day 30 because microcarriers were damaged. The tested concentrations of L-glutathione or L-methionine during runs 3 and 4 are shown in Table III. Working Day zero (WD0) is defined as the day during which the bioreactor is seeded. Production Day zero (PD0) is defined as the day during which the cell culture process is switch from growth phase to production phase. In addition, a run was performed without varying the antioxidant concentration. In this run, the L-methionine was added at 250 mg/L from the beginning (run 5). For all runs, the percentage of oxidized forms of rFSH was measured regularly (table IV).

TABLE III

Concentration of antioxidant in runs 3 and 4

| | Run 3 | Run 4 |
|---|---|---|
| Growth phase WD0 | No L-glutathione | L-methionine 50 mg/L |
| Growth phase WD1 up to PD0 (not included) | L-glutathione 1 mg/L | L-methionine 250 mg/L |
| PD0-PD9 | L-glutathione 1 mg/L | L-methionine 250 mg/L |
| PD10-PD19 | L-glutathione 2.5 mg/L | L-methionine 500 mg/L |

TABLE III-continued

Concentration of antioxidant in runs 3 and 4

| | Run 3 | Run 4 |
|---|---|---|
| PD20-PD29 | L-glutathione 5 mg/L | L-methionine 1000 mg/L |
| PD30-PD39 | L-glutathione 10 mg/L | L-methionine 2000 mg/L |
| PD40-PD49 | L-glutathione 20 mg/L | L-methionine 3000 mg/L |

TABLE IV

Effect of antioxidants on the oxidized forms of rFSH

| WD at which the oxidized forms were measured | Antioxidant | Mean concentration (mg/L) | % oxidized forms |
|---|---|---|---|
| Run 3 | | | |
| WD19 | L-glutathione | 1 | 18.31 |
| WD28 | L-glutathione | 2.5 | 14.26 |
| WD40 | L-glutathione | 5 | 23.99 |
| Run 4 | | | |
| WD19 | L-methionine | 250 | 15.37 |
| WD28 | L-methionine | 500 | 14.26 |
| WD40 | L-methionine | 1000 | 13.56 |
| WD49 | L-methionine | 2000 | 9.77 |
| WD59 | L-methionine | 3000 | 12.66 |

TABLE IV-continued

Effect of antioxidants on the oxidized forms of rFSH

| WD at which the oxidized forms were measured | Antioxidant | Mean concentration (mg/L) | % oxidized forms |
|---|---|---|---|
| Run 5 | | | |
| WD16-17 | L-methionine | 250 mg/L | 16.91 |
| WD20-21 | | | 14.45 |
| WD22-23 | | | 12.94 |
| WD24-25 | | | 12.16 |
| WD26-27 | | | 10.54 |
| WD28-29 | | | 12.83 |
| WD30-31 | | | 13.21 |

The analyses of oxidized rFSH forms when antioxidant was added to the culture medium showed that L-methionine is a good antioxidant. In run 5, wherein the cells were cultivated in the presence of L-methionine at 250 mg/L, the average percentage of oxidized forms was decreased by around 40% as compared to the results obtained in run 1 and run 2 with L-cysteine as antioxidant (see Table II & IV). L-Glutathione is a good antioxidant as well, especially at a concentration of about 2.5 mg/L. In run 3, the percentage of oxidized forms was decreased by around 35% when the cells were cultivated in the presence of L-glutathione at 2.5 mg/L, as compared to the results obtained in run 1 and run 2 with L-cysteine as antioxidant (see Table II & IV).

Increasing concentrations of L-methionine seem to have a decreasing trend on the percentage of oxidized forms between 250 and 2000 mg/L in run 4. However, it appears that the differences observed are within the method variability as comparable variations were observed in Run 5 testing one L-methionine concentration of 250 mg/L for the whole run. In addition, it was confirmed that L-glutathione and L-methionine did not have any major impact on viability of the cells, metabolism and productivity patterns in the range of concentration that was tested (data not shown).

REFERENCES

1. Altschul, S. F., Gish, W., Miller, W., Myers, E. W., and Lipman, D. J. (1990). Basic local alignment search tool. J. Mol. Biol. 215, 403-410.
2. Altschul, S. F., Madden, T. L., Schaffer, A A., Zhang, J., Zhang, Z., Miller, W., and Lipman, D. J. (1997). Gapped BLAST and PSI-BLAST: a new generation of protein database search programs. Nucleic Acids Res. 25, 3389-3402.
3. Bassett, R. M. and Driebergen, R. (2005). Continued improvements in the quality and consistency of follitropin alfa, recombinant human FSH. Reprod. Biomed. Online. 10, 169-177.
4. Brutlag, D. L., Dautricourt, J. P., Maulik, S., and Relph, J. (1990). Improved sensitivity of biological sequence database searches. Comput. Appl. Biosci. 6, 237-245.
5. Gonnet, G. H., Cohen, M. A., and Benner, S. A. (1992). Exhaustive matching of the entire protein sequence database. Science 256, 1443-1445.
6. Grantham, R. (1974). Amino acid difference formula to help explain protein evolution. Science 185, 862-864.
7. Henikoff, S. and Henikoff, J. G. (1993). Performance evaluation of amino acid substitution matrices. Proteins 17, 49-61.
8. Higgins, D. G., Thompson, J. D., and Gibson, T. J. (1996). Using CLUSTAL for multiple sequence alignments. Methods Enzymol. 266, 383-402.
9. Karlin, S. and Altschul, S. F. (1990). Methods for assessing the statistical significance of molecular sequence features by using general scoring schemes. Proc. Natl. Acad. Sci. U. S. A 87, 2264-2268.
10. LaPolt, P. S., Nishimori, K., Fares, F. A., Perlas, E., Boime, I., and Hsueh, A. J. (1992). Enhanced stimulation of follicle maturation and ovulatory potential by long acting follicle-stimulating hormone agonists with extended carboxyl-terminal peptides. Endocrinology 131, 2514-2520.
11. Matzuk, M. M., Kornmeier, C. M., Whitfield, G. K., Kourides, I. A., and Boime, I. (1988). The glycoprotein alpha-subunit is critical for secretion and stability of the human thyrotropin beta-subunit. Mol. Endocrinol. 2, 95-100.
12. Pearson, W. R. and Lipman, D. J. (1988). Improved tools for biological sequence comparison. Proc. Natl. Acad. Sci. U. S. A 85, 2444-2448.
13. Saito, Y., Yoshida, Y., Akazawa, T., Takahashi, K., and Niki, E. (2003). Cell death caused by selenium deficiency and protective effect of antioxidants. J. Biol. Chem. 278, 39428-39434.
14. Skrabanja, A. and Van den Oetelaar, P. Liquid gonadotropin containing formulations. EP 0 853 945 A1. 22-7-1998.
15. Takruri H. Method for the stabilisation of methionine-containing polypeptides. WO 92/15614. 17-9-1992.
16. Talmadge, K., Boorstein, W. R., and Fiddes, J. C. (1983). The human genome contains seven genes for the beta-subunit of chorionic gonadotropin but only one gene for the beta-subunit of luteinizing hormone. DNA 2, 281-289.
17. Thompson, J. D., Higgins, D. G., and Gibson, T. J. (1994). CLUSTAL W: improving the sensitivity of progressive multiple sequence alignment through sequence weighting, position-specific gap penalties and weight matrix choice. Nucleic Acids Res. 22, 4673-4680.
18. Yun, Z., Takagi, M., and Yoshida, T. (2003). Combined addition of glutathione and iron chelators for decrease of intracellular level of reactive oxygen species and death of Chinese hamster ovary cells. J. Biosci. Bioeng. 95, 124-127.

The invention claimed is:

1. A serum-free culture medium for the production of recombinant dimeric gonadotropins comprising, as an antioxidant, a combination of ascorbic acid at a concentration of about 30 mg/L and of (+)-alpha-tocopherol at a concentration of about 14 mg/L.

2. The culture medium according to claim 1, wherein said culture medium is a chemically defined medium.

3. The culture medium according to claim 1, wherein said culture medium is selected from the group consisting of SFM 90, SFM 90.1, SupMed300, DMEM, DMEM/F12, SFM CHO 3a, CHP PFM, ProCHO 5, EX-CELL, CHO-CD3, CHO III PFM, CHO-S-SFM II, CHO-DHFR, SFM4CHO, Ultra CHO, HyQ PF CHO, HyQ SFX CHO, HyQ CDM4CHO, IS CHO-CD, IS CHO-V, and derivatives thereof.

4. The culture medium according to claim 1, wherein said culture medium further comprises host cells expressing recombinant dimeric gonadotropins.

5. A method of reducing the levels of oxidized forms of a recombinant dimeric gonadotropin during its manufacturing process comprising cultivating cells expressing said recombinant dimeric gonadotropin in a serum-free culture medium according to claim 1.

6. The method according to claim 5, wherein said manufacturing process comprises the step of collecting the medium comprising said recombinant dimeric gonadotropin.

7. The method according to claim 5, wherein said manufacturing process comprises the step of purifying said recombinant dimeric gonadotropin.

8. The method according to claim 7, wherein said manufacturing process further comprises the step of formulating said recombinant dimeric gonadotropin into a pharmaceutical composition.

9. The method according to claim 5, wherein said gonadotropin is FSH.

10. The method according to claim 5, wherein said recombinant dimeric gonadotropin is produced in CHO cells.

11. The method according to claim 5, wherein said culture medium is a chemically defined medium.

12. The method according to claim 5, wherein said culture medium is selected from the group consisting of SFM 90, SFM 90.1, SupMed300, DMEM, DMEM/F12, SFM CHO 3a, CHP PFM, ProCHO 5, EX-CELL, CHO-CD3, CHO III PFM, CHO-S-SFM II, CHO-DHFR, SFM4CHO, Ultra CHO, HyQ PF CHO, HyQ SFX CHO, HyQ CDM4CHO, IS CHO-CD, IS CHO-V, and derivatives thereof.

* * * * *

UNITED STATES PATENT AND TRADEMARK OFFICE
CERTIFICATE OF CORRECTION

PATENT NO. : 8,093,052 B2
APPLICATION NO. : 11/994885
DATED : January 10, 2012
INVENTOR(S) : Jean-Pierre Fonta et al.

Page 1 of 1

It is certified that error appears in the above-identified patent and that said Letters Patent is hereby corrected as shown below:

Title Page,
Item (57) Abstract, Line 7, "(+)-alpha-toc0plierol" should read --(+)-alpha-tocopherol--.

Column 3,
Line 12, "surpernatant" should read --supernatant--.

Column 9,
Table 1, Column "Medium", "L-GLUTHATIONE" should read
--L-GLUTATHIONE--.

Column 18,
Lines 40-41, "$GCR=(G_0-G_t)D_t+(G_{t-1}-G_t)$" should read
--$GCR=(G_0-G_t)\cdot D_t+(G_{t-1}-G_t)$--.

Column 19,
Line 56, "and. Run 3," should read --and run 3,--.
Line 62, "is switch" should read --is switched--.

Column 23,
Line 8, "according to claim 5" should read --according to claim 7--.

Signed and Sealed this
Twenty-eighth Day of August, 2012

David J. Kappos
*Director of the United States Patent and Trademark Office*